(12) United States Patent
Gunji et al.

(10) Patent No.: US 7,335,506 B2
(45) Date of Patent: *Feb. 26, 2008

(54) METHOD FOR PRODUCING L-LYSINE OR L-ARGININE BY USING METHANOL-ASSIMILATING BACTERIUM

(75) Inventors: Yoshiya Gunji, Kanagawa (JP); Hisashi Yasueda, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 422 days.

This patent is subject to a terminal disclaimer.

(21) Appl. No.: 10/716,470

(22) Filed: Nov. 20, 2003

(65) Prior Publication Data

US 2005/0003495 A1    Jan. 6, 2005

(30) Foreign Application Priority Data

Nov. 20, 2002 (JP) .............................. 2002-336340

(51) Int. Cl.
*C12N 1/20* (2006.01)
*C12P 13/08* (2006.01)
*C12P 13/04* (2006.01)
*C12P 13/10* (2006.01)
*C12P 21/06* (2006.01)
*C12N 15/00* (2006.01)
*C07K 14/00* (2006.01)
*C07H 21/00* (2006.01)

(52) U.S. Cl. .............................. 435/252.31; 435/252.3; 435/115; 435/106; 435/69.1; 435/320.1; 435/114; 530/350; 536/23.1

(58) Field of Classification Search ............ 435/252.3, 435/252.31, 115, 106, 69.1, 320.1, 116; 530/350; 536/23.1

See application file for complete search history.

(56) References Cited

U.S. PATENT DOCUMENTS

| | | | |
|---|---|---|---|
| 3,907,637 A | 9/1975 | Nakayama et al. | ........... 195/29 |
| 3,907,641 A | 9/1975 | Nakayama et al. | ........... 195/49 |
| 5,217,883 A | 6/1993 | Anazawa et al. | ........ 435/252.3 |
| 5,972,663 A | 10/1999 | Winterhalter et al. | .. 435/252.32 |
| 6,461,852 B1 | 10/2002 | Tsujimoto et al. | |
| 2003/0013174 A1 | 1/2003 | Tsujimoto et al. | |
| 2003/0049805 A1 | 3/2003 | Nagase et al. | |
| 2003/0124687 A1 | 7/2003 | Gunji et al. | |
| 2003/0166174 A1 | 9/2003 | Ono et al. | |
| 2003/0232338 A1 | 12/2003 | Usuda et al. | |
| 2004/0142435 A1 | 7/2004 | Gunji et al. | |
| 2004/0146974 A1 | 7/2004 | Gunji | |
| 2004/0166570 A1 | 8/2004 | Yasueda et al. | |
| 2004/0170985 A1 | 9/2004 | Usuda et al. | |
| 2004/0170986 A1 | 9/2004 | Usuda et al. | |
| 2004/0170987 A1 | 9/2004 | Usuda et al. | |
| 2004/0171134 A1 | 9/2004 | Yasueda et al. | |
| 2004/0191875 A1 | 9/2004 | Takeshita et al. | |
| 2004/0214296 A1 | 10/2004 | Asahara et al. | |

2004/0229311 A1    11/2004   Hirano et al.

FOREIGN PATENT DOCUMENTS

| | | |
|---|---|---|
| AU | 724536 | 9/2000 |
| AU | 200039386 | 4/2001 |
| EP | 1016710 | 7/2000 |
| EP | 1 067 193 | 1/2001 |
| EP | 1188822 | 3/2002 |
| JP | 45-25273 | 8/1970 |
| JP | 50-25790 | 3/1975 |
| JP | 52-18886 | 2/1977 |
| WO | WO90/12105 | 10/1990 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sousa et al., Microbiology 148(Pt5):1291-1303, 2002.*
Weaver et al., J. Bacteriol. 172(11):6581-6584, 1990.*
U.S. Appl. No. 09/926,299, filed Oct. 9, 2001, Gunji et al.
U.S. Appl. No. 10/791,853, filed Mar. 4, 2004, Takeshita et al.
Motoyama H. et al., "Characterization of the Aspartate Family Amino Acids Biosynthetic Enzymes in L-Threonine-and L-Lysine-producing Mutants of *Methylobacillus glycogenes*", Biosci. Biotech. Biochem., 1993, p. 461-466, vol. 57, No. 3.
H. Motoyama et al., "Overproduction of L-Lysine from Methanol by *Methylobacillus glycogenes* Derivatives Carrying a Plasmid with a Mutated *dapA* Gene", Applied and Environmental Microbiology, 2001, p. 3064-3070, vol. 67, No. 7.
French Search Report, Jul. 30, 2004, French Patent Office, FR 0313575.
Marina Vrljic et al., A new type of transporter with a new type of cellular function: L-lysine export from *Corynebacterium glutamicum*, Molecular Microbiology, 1996, p. 815-826, vol. 22, No. 5.
H. Motoyama et al., Effects of the amplification of the genes coding for the L-threonine biosynthesis enzymes on the L-threonine production from methanol by a gram-negative obligate methylotroph, *Methylobacillus glycogens*, Appl. Microbiol. Biotechnol., 1994, p. 67-72, vol. 42.
L. V. Kletsova et al., Mutants of the obligate methylotroph *Methylobacillus flagellatum* KT defective in genes of the ribulose monophosphate cycle of formaldehyde fixation, Arch. Microbiol., 1988, p. 441-446, vol. 149.

(Continued)

*Primary Examiner*—Delia M. Ramirez
(74) *Attorney, Agent, or Firm*—Shelly Guest Cermak; Cermak Kenealy & Vaidya LLP

(57) ABSTRACT

A DNA encoding a variant of a protein, the protein having a loop region and six hydrophobic helices and involved in secretion of L-lysine to the outside of a cell, wherein the DNA encodes a variant of a protein not containing the loop region and facilitates secretion of L-lysine, L-arginine or both of these L-amino acids to the outside of a methanol-assimilating bacterium when the DNA is introduced into the bacterium, specifically lysE24, is introduced into a *Methylobacillus* bacteria to improve L-amino acid productivity, especially L-lysine and L-arginine productivities.

6 Claims, 2 Drawing Sheets

OTHER PUBLICATIONS

Neil R. Wyborn et al., Molecular characterization of formamidase from *Methylophilus methylotrophus*, Eur. J. Biochem., 1996, p. 314-322, vol. 240.

A. Bellmann et al., Expression control and specificity of the basic amino acid exporter LysE of *Corynebacterium glutamicum*: Microbiology, 2001, p. 1765-1774, vol. 147.

Owen Jenkins et al., *Methylophilus*: a New Genus of Methanol-Utilizing Bacteria, International Journal of Systematic Bacteriology, Oct. 1987, p. 446-448, vol. 37, No. 4.

Téizi Urakami et al., Emendation of *Methylobacillus*: Yordy and Weaver 1977, a Genus for Methanol-Utilizing Bacteria, International Journal of Systematic Bacteriology, Oct. 1986, p. 502-511, vol. 36, No. 4.

\* cited by examiner

SEQUENCE LISTING

<160> NUMBER OF SEQ ID NOS: 14

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 1
agggaattcc ccgttctgga taatgttttt tgcgccgac                    39

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 2
cggatgcatc tagagttaac ctgcagggtg aaattgttat ccgctcacaa ttccacac    58

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 3
tgacctgcag gtttgcacag aggatggccc atgtt                        35

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 4
cattctagat ccctaaactt tacagcaaac cggcat                       36

<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 5
catttcctgc aggcaaagga gatgagcgta atggtgatca tggaaatctt cattacaggt    60
ctgc                                                          64

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 6
gggcgagcta gaagagctcc aaaacccgcg aaaactaacc catcaacatc          50

<210> SEQ ID NO 7
<211> LENGTH: 711
<212> TYPE: DNA
<213> ORGANISM: Brevibacterium lactofermentum
<220> FEATURE:
<221> NAME/KEY: CDS
<222> LOCATION: (1)..(711)

<400> SEQUENCE: 7

| | | | | | | | | | | | | | | | |
|---|---|---|---|---|---|---|---|---|---|---|---|---|---|---|---|
| atg | gtg | atc | atg | gaa | atc | ttc | att | aca | ggt | ctg | ctt | ttg | ggg | gcc | agt | 48 |
| Met | Val | Ile | Met | Glu | Ile | Phe | Ile | Thr | Gly | Leu | Leu | Leu | Gly | Ala | Ser | |
| 1 | | | | 5 | | | | | 10 | | | | | 15 | | |

| ctt | tta | ctg | tcc | atc | gga | ccg | cag | aat | gta | ctg | gtg | att | aaa | caa | gga | 96 |
|---|---|---|---|---|---|---|---|---|---|---|---|---|---|---|---|---|
| Leu | Leu | Leu | Ser | Ile | Gly | Pro | Gln | Asn | Val | Leu | Val | Ile | Lys | Gln | Gly | |
| | | | 20 | | | | | 25 | | | | | 30 | | | |

| att | aag | cgc | gaa | gga | ctc | att | gcg | gtt | ctt | ctc | gtg | tgt | tta | att | tct | 144 |
|---|---|---|---|---|---|---|---|---|---|---|---|---|---|---|---|---|
| Ile | Lys | Arg | Glu | Gly | Leu | Ile | Ala | Val | Leu | Leu | Val | Cys | Leu | Ile | Ser | |
| | | 35 | | | | | 40 | | | | | 45 | | | | |

| gac | gtc | ttt | ttg | ttc | atc | gcc | ggc | acc | ttg | ggc | gtt | gat | ctt | ttg | tcc | 192 |
|---|---|---|---|---|---|---|---|---|---|---|---|---|---|---|---|---|
| Asp | Val | Phe | Leu | Phe | Ile | Ala | Gly | Thr | Leu | Gly | Val | Asp | Leu | Leu | Ser | |
| 50 | | | | | 55 | | | | | 60 | | | | | | |

| aat | gcc | gcg | ccg | atc | gtg | ctc | gat | att | atg | cgc | tgg | ggt | ggc | atc | gct | 240 |
|---|---|---|---|---|---|---|---|---|---|---|---|---|---|---|---|---|
| Asn | Ala | Ala | Pro | Ile | Val | Leu | Asp | Ile | Met | Arg | Trp | Gly | Gly | Ile | Ala | |
| 65 | | | | | 70 | | | | | 75 | | | | | 80 | |

| tac | ctg | tta | tgg | ttt | gcc | gtc | atg | gca | gcg | aaa | gac | gcc | atg | aca | aac | 288 |
|---|---|---|---|---|---|---|---|---|---|---|---|---|---|---|---|---|
| Tyr | Leu | Leu | Trp | Phe | Ala | Val | Met | Ala | Ala | Lys | Asp | Ala | Met | Thr | Asn | |
| | | | | 85 | | | | | 90 | | | | | 95 | | |

| aag | gtg | gaa | gcg | cca | cag | atc | att | gaa | gaa | aca | gaa | cca | acc | gtg | ccc | 336 |
|---|---|---|---|---|---|---|---|---|---|---|---|---|---|---|---|---|
| Lys | Val | Glu | Ala | Pro | Gln | Ile | Ile | Glu | Glu | Thr | Glu | Pro | Thr | Val | Pro | |
| | | | 100 | | | | | 105 | | | | | 110 | | | |

| gat | gac | acg | cct | ttg | ggc | ggt | tcg | gcg | gtg | gcc | act | gac | acg | cgc | aac | 384 |
|---|---|---|---|---|---|---|---|---|---|---|---|---|---|---|---|---|
| Asp | Asp | Thr | Pro | Leu | Gly | Gly | Ser | Ala | Val | Ala | Thr | Asp | Thr | Arg | Asn | |
| | | 115 | | | | | 120 | | | | | 125 | | | | |

| cgg | gtg | cgg | gtg | gag | gtg | agc | gtc | gat | aag | cag | cgg | gtt | tgg | gta | aag | 432 |
|---|---|---|---|---|---|---|---|---|---|---|---|---|---|---|---|---|
| Arg | Val | Arg | Val | Glu | Val | Ser | Val | Asp | Lys | Gln | Arg | Val | Trp | Val | Lys | |
| | 130 | | | | | 135 | | | | | 140 | | | | | |

| ccc | atg | ttg | atg | gca | atc | gtg | ctg | acc | tgg | ttg | aac | ccg | aat | gcg | tat | 480 |
|---|---|---|---|---|---|---|---|---|---|---|---|---|---|---|---|---|
| Pro | Met | Leu | Met | Ala | Ile | Val | Leu | Thr | Trp | Leu | Asn | Pro | Asn | Ala | Tyr | |
| 145 | | | | | 150 | | | | | 155 | | | | | 160 | |

| ttg | gac | gcg | ttt | gtg | ttt | atc | ggc | ggc | gtc | ggc | gcg | caa | tac | ggc | gac | 528 |
|---|---|---|---|---|---|---|---|---|---|---|---|---|---|---|---|---|
| Leu | Asp | Ala | Phe | Val | Phe | Ile | Gly | Gly | Val | Gly | Ala | Gln | Tyr | Gly | Asp | |
| | | | | 165 | | | | | 170 | | | | | 175 | | |

| acc | gga | cgg | tgg | att | ttc | gcc | gct | ggc | gcg | ttc | gcg | gca | agc | ctg | atc | 576 |
|---|---|---|---|---|---|---|---|---|---|---|---|---|---|---|---|---|
| Thr | Gly | Arg | Trp | Ile | Phe | Ala | Ala | Gly | Ala | Phe | Ala | Ala | Ser | Leu | Ile | |
| | | | 180 | | | | | 185 | | | | | 190 | | | |

| tgg | ttc | ccg | ctg | gtg | ggt | ttc | ggc | gca | gca | gca | ttg | tca | cgc | ccg | ctg | 624 |
|---|---|---|---|---|---|---|---|---|---|---|---|---|---|---|---|---|
| Trp | Phe | Pro | Leu | Val | Gly | Phe | Gly | Ala | Ala | Ala | Leu | Ser | Arg | Pro | Leu | |
| | | 195 | | | | | 200 | | | | | 205 | | | | |

| tcc | agc | ccc | aag | gtg | tgg | cgc | tgg | atc | aac | gtc | gtc | gtg | gca | gtt | gtg | 672 |
|---|---|---|---|---|---|---|---|---|---|---|---|---|---|---|---|---|
| Ser | Ser | Pro | Lys | Val | Trp | Arg | Trp | Ile | Asn | Val | Val | Val | Ala | Val | Val | |
| | 210 | | | | | 215 | | | | | 220 | | | | | |

| atg | acc | gca | ttg | gcc | atc | aaa | ctg | atg | ttg | atg | ggt | tag | | | | 711 |
|---|---|---|---|---|---|---|---|---|---|---|---|---|---|---|---|---|
| Met | Thr | Ala | Leu | Ala | Ile | Lys | Leu | Met | Leu | Met | Gly | | | | | |
| 225 | | | | | 230 | | | | | 235 | | | | | | |

<210> SEQ ID NO 8
<211> LENGTH: 236
<212> TYPE: PRT
<213> ORGANISM: Brevibacterium lactofermentum

<400> SEQUENCE: 8

Met Val Ile Met Glu Ile Phe Ile Thr Gly Leu Leu Leu Gly Ala Ser

```
                1               5              10              15
              Leu Leu Leu Ser Ile Gly Pro Gln Asn Val Leu Val Ile Lys Gln Gly
                           20                  25                  30

Ile Lys Arg Glu Gly Leu Ile Ala Val Leu Leu Val Cys Leu Ile Ser
                           35                  40                  45

Asp Val Phe Leu Phe Ile Ala Gly Thr Leu Gly Val Asp Leu Leu Ser
                           50                  55                  60

Asn Ala Ala Pro Ile Val Leu Asp Ile Met Arg Trp Gly Gly Ile Ala
               65                  70                  75                  80

Tyr Leu Leu Trp Phe Ala Val Met Ala Ala Lys Asp Ala Met Thr Asn
                                   85                  90                  95

Lys Val Glu Ala Pro Gln Ile Ile Glu Glu Thr Glu Pro Thr Val Pro
                                  100                 105                 110

Asp Asp Thr Pro Leu Gly Gly Ser Ala Val Ala Thr Asp Thr Arg Asn
                          115                 120                 125

Arg Val Arg Val Glu Val Ser Val Asp Lys Gln Arg Val Trp Val Lys
                          130                 135                 140

Pro Met Leu Met Ala Ile Val Leu Thr Trp Leu Asn Pro Asn Ala Tyr
              145                 150                 155                 160

Leu Asp Ala Phe Val Phe Ile Gly Gly Val Gly Ala Gln Tyr Gly Asp
                                  165                 170                 175

Thr Gly Arg Trp Ile Phe Ala Ala Gly Ala Phe Ala Ala Ser Leu Ile
                                  180                 185                 190

Trp Phe Pro Leu Val Gly Phe Gly Ala Ala Ala Leu Ser Arg Pro Leu
                                  195                 200                 205

Ser Ser Pro Lys Val Trp Arg Trp Ile Asn Val Val Ala Val Val
                          210                 215                 220

Met Thr Ala Leu Ala Ile Lys Leu Met Leu Met Gly
              225                 230                 235

<210> SEQ ID NO 9
<211> LENGTH: 712
<212> TYPE: DNA
<213> ORGANISM: Brevibacterium lactofermentum
<220> FEATURE:
<221> NAME/KEY: CDS
<222> LOCATION: (1)..(375)

<400> SEQUENCE: 9 atg gtg atc atg gaa atc ttc att aca ggt ctg ctt ttg ggg gcc agt      48
Met Val Ile Met Glu Ile Phe Ile Thr Gly Leu Leu Leu Gly Ala Ser
  1               5                  10                  15 ctt ttg ctg tcc atc gga ccg cag aat gta ctg gtg att aaa caa gga      96
Leu Leu Leu Ser Ile Gly Pro Gln Asn Val Leu Val Ile Lys Gln Gly
             20                  25                  30 att aag cgc gaa gga ctc att gcg gtt ctt ctc gtg tgt tta att tct     144
Ile Lys Arg Glu Gly Leu Ile Ala Val Leu Leu Val Cys Leu Ile Ser
             35                  40                  45 gac gtc ttt ttg ttc atc gcc ggc acc ttg ggc gtt gat ctt ttg tcc     192
Asp Val Phe Leu Phe Ile Ala Gly Thr Leu Gly Val Asp Leu Leu Ser
             50                  55                  60 aat gcc gcg ccg atc gtg ctc gat att atg cgc tgg ggt ggc atc gct     240
Asn Ala Ala Pro Ile Val Leu Asp Ile Met Arg Trp Gly Gly Ile Ala
 65                  70                  75                  80 tac ctg tta tgg ttt gcc gtc atg gca gcg aaa gac gcc atg aca aac     288
Tyr Leu Leu Trp Phe Ala Val Met Ala Ala Lys Asp Ala Met Thr Asn
                     85                  90                  95
```

```
aag gtg gaa gcg cca cag atc att gaa gaa aca gaa cca acc gtg ccc      336
Lys Val Glu Ala Pro Gln Ile Ile Glu Glu Thr Glu Pro Thr Val Pro
            100                 105                 110 gat gac acg cct ttg ggc gtg ttc ggc ggt ggc cac tga cacgcgcaac       385
Asp Asp Thr Pro Leu Gly Val Phe Gly Gly Gly His
        115                 120                 125 cgggtgcggg tggaggtgag cgtcgataag cagcgggttt gggtgaagcc catgttgatg    445
gcaatcgtgc tgacctggtt gaacccgaat gcgtatttgg acgcgtttgt gtttatcggc    505
ggcgtcggcg cgcaatacgg cgacaccgga cggtggattt cgccgctgg cgcgttcgcg     565 gcaagcctga tctggttccc gctggtgggt ttcggcgcag cagcattgtc acgcccgctg    625
tccagcccca aggtgtggcg ctggatcaac gtcgtcgtgg cagttgtgat gaccgcattg    685
gccatcaaac tgatgttgat gggttag                                        712

<210> SEQ ID NO 10
<211> LENGTH: 124
<212> TYPE: PRT
<213> ORGANISM: Brevibacterium lactofermentum

<400> SEQUENCE: 10

Met Val Ile Met Glu Ile Phe Ile Thr Gly Leu Leu Leu Gly Ala Ser
 1               5                  10                  15

Leu Leu Leu Ser Ile Gly Pro Gln Asn Val Leu Val Ile Lys Gln Gly
            20                  25                  30

Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
    50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
            100                 105                 110

Asp Asp Thr Pro Leu Gly Val Phe Gly Gly Gly His
        115                 120

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 11
aaagaattcg cacggatcac tgtattcggc tgcaacttt                            39

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 12
aaagaattcg ccgtgttgct aggatggttg ttcttggatc a                         41

<210> SEQ ID NO 13
<211> LENGTH: 1197
```

```
<212> TYPE: DNA
<213> ORGANISM: Escherichia coli
<220> FEATURE:
<221> NAME/KEY: CDS
<222> LOCATION: (272)..(1153)

<400> SEQUENCE: 13
ccaggcgact gtcttcaata ttacagccgc aactactgac atgacgggtg atggtgttca        60
caattccacg cgatcggca cccaacgcag tgatcaccag ataatgtgtt gcatgacag         120 tgtcaaactg gttattcctt taaggggtga gttgttctta aggaaagcat aaaaaaaaca       180
tgcatacaac aatcagaacg gttctgtctg cttgcttttta atgccatacc aaacgtacca      240
ttgagacact tgtttgcaca gaggatggcc c atg ttc acg gga agt att gtc          292
                                   Met Phe Thr Gly Ser Ile Val
                                    1               5 gcg att gtt act ccg atg gat gaa aaa ggt aat gtc tgt cgg gct agc          340
Ala Ile Val Thr Pro Met Asp Glu Lys Gly Asn Val Cys Arg Ala Ser
        10                  15                  20 ttg aaa aaa ctg att gat tat cat gtc gcc agc ggt act tcg gcg atc          388
Leu Lys Lys Leu Ile Asp Tyr His Val Ala Ser Gly Thr Ser Ala Ile
 25                  30                  35 gtt tct gtt ggc acc act ggc gag tcc gct acc tta aat cat gac gaa          436
Val Ser Val Gly Thr Thr Gly Glu Ser Ala Thr Leu Asn His Asp Glu
40                  45                  50                  55 cat gct gat gtg gtg atg atg acg ctg gat ctg gct gat ggg cgc att          484
His Ala Asp Val Val Met Met Thr Leu Asp Leu Ala Asp Gly Arg Ile
                60                  65                  70 ccg gta att gcc ggg acc ggc gct aac gct act gcg gaa gcc att agc          532
Pro Val Ile Ala Gly Thr Gly Ala Asn Ala Thr Ala Glu Ala Ile Ser
         75                  80                  85 ctg acg cag cgc ttc aat gac agt ggt atc gtc ggc tgc ctg acg gta          580
Leu Thr Gln Arg Phe Asn Asp Ser Gly Ile Val Gly Cys Leu Thr Val
 90                  95                 100 acc cct tac tac aat cgt ccg tcg caa gaa ggt ttg tat cag cat ttc          628
Thr Pro Tyr Tyr Asn Arg Pro Ser Gln Glu Gly Leu Tyr Gln His Phe
105                 110                 115 aaa gcc atc gct gag cat act gac ctg ccg caa att ctg tat aat gtg          676
Lys Ala Ile Ala Glu His Thr Asp Leu Pro Gln Ile Leu Tyr Asn Val
120                 125                 130                 135 ccg tcc cgt act ggc tgc gat ctg ctc ccg gaa acg gtg ggc cgt ctg          724
Pro Ser Arg Thr Gly Cys Asp Leu Leu Pro Glu Thr Val Gly Arg Leu
                140                 145                 150 gcg aaa gta aaa aat att atc gga atc aaa gag gca aca ggg aac tta          772
Ala Lys Val Lys Asn Ile Ile Gly Ile Lys Glu Ala Thr Gly Asn Leu
                155                 160                 165 acg cgt gta aac cag atc aaa gag ctg gtt tca gat gat ttt gtt ctg          820
Thr Arg Val Asn Gln Ile Lys Glu Leu Val Ser Asp Asp Phe Val Leu
            170                 175                 180 ctg agc ggc gat gat gcg agc gcg ctg gac ttc atg caa ttg ggc ggt          868
Leu Ser Gly Asp Asp Ala Ser Ala Leu Asp Phe Met Gln Leu Gly Gly
        185                 190                 195 cat ggg gtt att tcc gtt acg act aac gtc gca gcg cgt gat atg gcc          916
His Gly Val Ile Ser Val Thr Thr Asn Val Ala Ala Arg Asp Met Ala
200                 205                 210                 215 cag atg tgc aaa ctg gca gca gaa gaa cat ttt gcc gag gca cgc gtt          964
Gln Met Cys Lys Leu Ala Ala Glu Glu His Phe Ala Glu Ala Arg Val
                220                 225                 230 att aat cag cgt ctg atg cca tta cac aac aaa cta ttt gtc gaa ccc         1012
Ile Asn Gln Arg Leu Met Pro Leu His Asn Lys Leu Phe Val Glu Pro
            235                 240                 245
```

```
aat cca atc ccg gtg aaa tgg gca tgt aag gaa ctg ggt ctt gtg gcg      1060
Asn Pro Ile Pro Val Lys Trp Ala Cys Lys Glu Leu Gly Leu Val Ala
        250                 255                 260 acc gat acg ctg cgc ctg cca atg aca cca atc acc gac agt ggt cgt      1108
Thr Asp Thr Leu Arg Leu Pro Met Thr Pro Ile Thr Asp Ser Gly Arg
265                 270                 275 gag acg gtc aga gcg gcg ctt aag cat gcc ggt ttg ctg taa              1150
Glu Thr Val Arg Ala Ala Leu Lys His Ala Gly Leu Leu
280                 285                 290 agtttaggga gatttgatgg cttactctgt tcaaaagtcg cgcctgg                  1197

<210> SEQ ID NO 14
<211> LENGTH: 292
<212> TYPE: PRT
<213> ORGANISM: Escherichia coli

<400> SEQUENCE: 14

Met Phe Thr Gly Ser Ile Val Ala Ile Val Thr Pro Met Asp Glu Lys
 1               5                  10                  15

Gly Asn Val Cys Arg Ala Ser Leu Lys Lys Leu Ile Asp Tyr His Val
                20                  25                  30

Ala Ser Gly Thr Ser Ala Ile Val Ser Val Gly Thr Thr Gly Glu Ser
            35                  40                  45

Ala Thr Leu Asn His Asp Glu His Ala Asp Val Val Met Met Thr Leu
        50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Thr Asn
        195                 200                 205

Val Ala Ala Arg Asp Met Ala Gln Met Cys Lys Leu Ala Ala Glu Glu
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270
```

```
-continued

Pro Ile Thr Asp Ser Gly Arg Glu Thr Val Arg Ala Ala Leu Lys His
        275                 280                 285

Ala Gly Leu Leu
    290
```

METHOD FOR PRODUCING L-LYSINE OR L-ARGININE BY USING METHANOL-ASSIMILATING BACTERIUM

BACKGROUND OF THE INVENTION

1. Field of the Invention

The present invention relates to techniques useful in the microbial industry. More specifically, the present invention relates to a method for producing L-lysine or L-arginine by fermentation, and a microorganism used in the production method.

2. Background Art

Amino acids such as L-lysine, L-glutamic acid, L-threonine, L-leucine, L-isoleucine, L-valine and L-phenylalanine are industrially produced by fermentation using microorganisms that belong to the genus *Brevibacterium* (*Corynebacterium*), *Bacillus, Escherichia, Streptomyces, Pseudomonas, Arthrobacter, Serratia, Penicillium, Candida* or the like. Strains isolated from nature, or artificial mutants thereof, have been used to improve the productivity of these microorganisms. Moreover, various techniques have been disclosed for increasing the L-amino acid producing abilities, such as recombinant DNA techniques to enhance L-amino acid biosynthetic enzymes.

Production of L-amino acids has been considerably increased by breeding of microorganisms such as those mentioned above with improved production methods. However, in order to respond to further increases in demand in future, development of methods which provide more efficient production of L-amino acids at lower cost are clearly still necessary, and therefore, still represent a need in the art.

Methanol is a known fermentation raw material which is available in large amounts at a low cost. Methods for producing L-amino acids by fermentation using methanol are known, and include methods using microorganisms that belong to the genus *Achromobacter* or *Pseudomonas* (Japanese Patent Publication (Kokoku) No. 45-25273), *Protaminobacter* (Japanese Patent Laid-open (Kokai) No. 49-125590), *Protaminobacter* or *Methanomonas* (Japanese Patent Laid-open No. 50-25790), *Microcyclus* (Japanese Patent Laid-open No. 52-18886), *Methylobacillus* (Japanese Patent Laid-open No. 4-91793), *Bacillus* (Japanese translation of PCT international application Patent (Kohyo) No. 3-505284) (WO90/12105) and so forth. The inventors of the present invention have developed methods for producing L-amino acids by breeding *Methylophilus* bacteria using artificial mutagenesis and recombinant DNA techniques (WO 00/61723).

In recent years, proteins have been identified that have a function of specifically secreting an L-amino acid to the outside a cell of microorganism, as well as genes which encode these proteins. In particular, Vrljic et al. have identified a gene involved in secretion of L-lysine derived from *Corynebacterium glutamicum* R127 to the outside of a cell (Vrljic M., Sahm H., Eggeling L., Molecular Microbiology 22:815-826 (1996)). This gene was designated as lysE, and it was reported that L-lysine producing ability of *Corynebacterium* bacteria could be improved by enhancing the expression of this gene in *Corynebacterium* bacteria (WO97/23597). The gene lysE is known to secrete not only L-lysine, but also L-arginine (Bellmann A., Vrljic M., Patek M., Sahm H., Kramer R., Eggeling L. Microbiology, 147: 1765-1774 (2001)). It is also known that production of some L-amino acids can be improved by increasing expression amounts of amino acid secreting proteins in *Escherichia coli* (Japanese Patent Laid-open No. 2000-189180). For example, it is reported that production of cystine, cysteine, and so forth can be improved by enhancing the expression of ORF306 gene in *Escherichia coli* (EP885962).

However, there have been no reports to date suggesting that the amino acid secretion process is involved either positively or negatively in amino acid production by fermentation of methanol using a methanol-assimilating bacterium. There have also been no reports suggesting an amino acid secretion gene that can provide secretion activity in a methanol-assimilating bacterium.

SUMMARY OF THE INVENTION

An object of the present invention is to provide a method for efficiently producing L-lysine or L-arginine using methanol, which is abundantly and inexpensively available.

It is a further object of the present invention to provide a bacterium belonging to the genus *Methylobacillus*, into which a DNA which is able to be expressed is introduced, and said bacterium having an ability to produce L-lysine or L-arginine, wherein said DNA encodes a variant of a protein, the protein having a loop region and six hydrophobic helices and is involved in secretion of L-lysine to the outside of a cell, and wherein said variant does not contain said loop region and facilitates secretion of L-lysine, L-arginine or both to the outside of a methanol-assimilating bacterium when said DNA is introduced into said methanol-assimilating bacterium.

It is even a further object of the present invention to provide the bacterium as described above, wherein said mutant protein substantially consists of only the hydrophobic helices.

It is even a further object of the present invention to provide the bacterium as described above, wherein said variant has six hydrophobic helices.

It is even a further object of the present invention to provide the bacterium as described above, wherein said variant is a complex comprising a peptide containing the first, second, and third hydrophobic helices relative to the N-terminus, and a peptide containing the fourth, fifth, and sixth hydrophobic helices relative to the N-terminus.

It is even a further object of the present invention to provide the bacterium as described above, wherein the protein is LysE protein.

It is even a further object of the present invention to provide the bacterium as described above, wherein said LysE protein is derived from a coryneform bacterium.

It is even a further object of the present invention to provide a bacterium belonging to the genus *Methylobacillus*, into which a DNA which is able to be expressed is introduced, and which has an ability to produce L-lysine or L-arginine, wherein said DNA encodes a protein selected from the group consisting of:

(A) a protein which comprises the amino acid sequence of SEQ ID NO: 10, and (B) a protein which comprises the amino acid sequence of SEQ ID NO: 10 including substitution, deletion, insertion or addition of one or several amino acid residues, and wherein said protein shows an activity for facilitating secretion of L-lysine, L-arginine or both to the outside of a methanol-assimilating bacterium.

It is even a further object of the present invention to provide a method for producing L-lysine or L-arginine, comprising culturing the bacterium belonging to the genus *Methylobacillus* as described above in a medium to produce and accumulate L-lysine or L-arginine in culture, and collecting L-lysine or L-arginine from the culture.

It is even a further object of the present invention to provide the method for producing L-lysine or L-arginine as described above, wherein the medium contains methanol as a main carbon source.

According to the present invention, L-amino acid production, especially L-lysine and L-arginine, using a methanol-assimilating bacterium can be improved.

DESCRIPTION OF THE PREFERRED EMBODIMENTS

Figure 1:
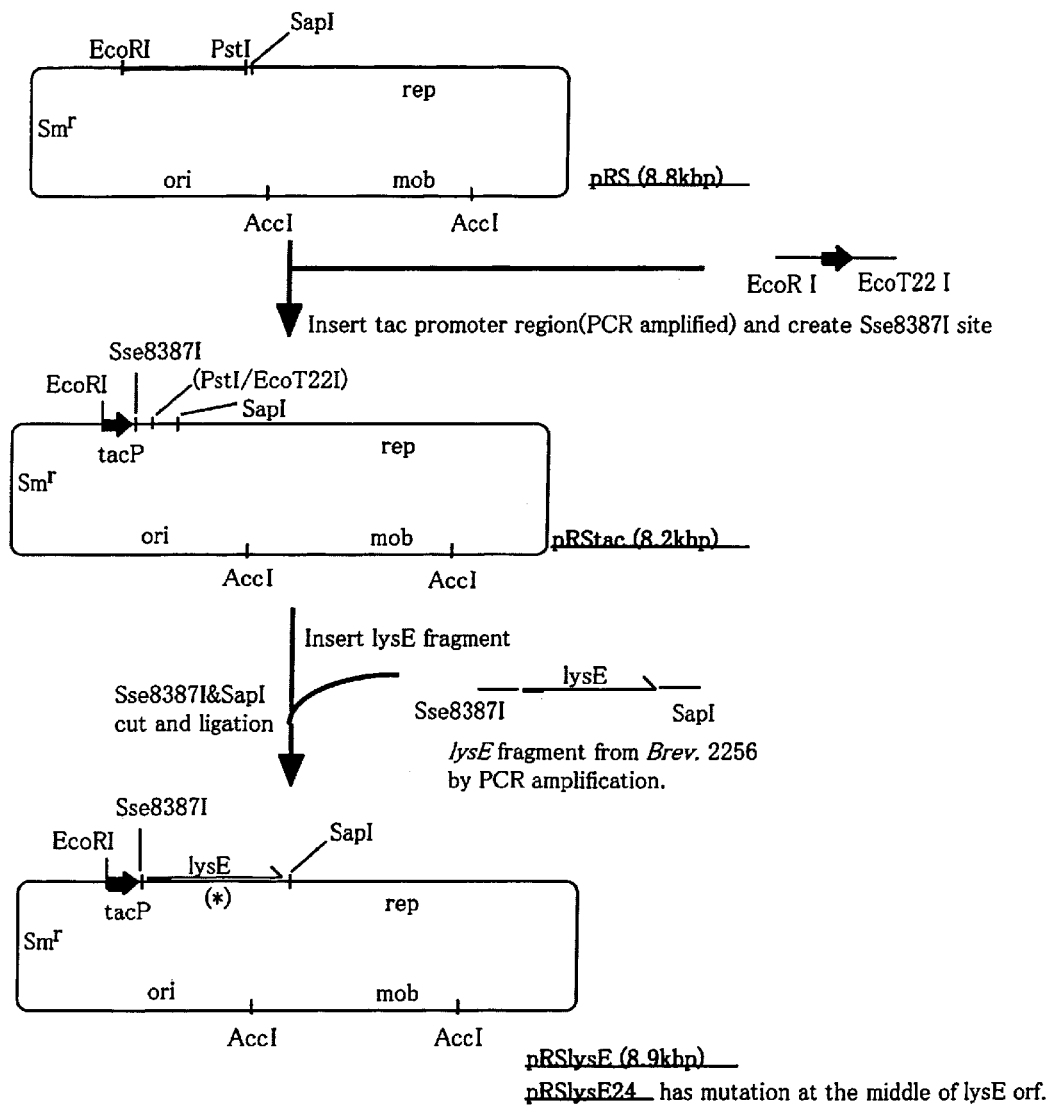
FIG. 1 shows constructions of a plasmid pRStac having the tac promoter and plasmids pRSlysE and pRSlysE24 consisting of the plasmid pRStac inserted with the lysE gene or lysE24 gene.

The inventors of the present invention assiduously studied in order to achieve the aforementioned objects. Initially, they found L-amino acid production by methanol-assimilating bacterium, especially *Methylobacillus* bacterium, was not possible due to failure of the L-amino acid secretion process to the outside of cells. Then, they successfully isolated a gene that provided amino acid secretion activity, especially in the microorganism, which aided in enabling efficient amino acid production.

The inventors of the present invention introduced a gene derived from a *Brevibacterium lactofermentum* 2256 strain, which is a homologue of the known lysE gene from a *Corynebacterium glutamicum* R127, into a methanol-assimilating bacterium and investigated its effect on amino acid production.

It shoud be noted that bacteria which was classified into the genus *Brevibacterium* has been united into the genus *Corynebacterium* (Int. J. Syst. Bacteriol., 41, 255 (1981)).

It was found that introduction of the lysE gene into a methanol-assimilating bacterium resulted in a mutation or deletion, and thus LysE protein could not function. Proteins responsible for secretion typically need to be incorporated into the cell membrane in order to function, therefore, the protein and membrane conditions such as lipid composition must be suitable for each other. It was concluded that it would be difficult to express a heterologous membrane protein, such as LysE, so that the protein can function, and this conclusion was supported by the aforementioned result.

Therefore, the inventors of the present invention found a mutant gene that could function in a methanol-assimilating bacterium while researching the aforementioned L-amino acid secretion genes. Furthermore, they found a marked effect upon use of this mutant gene in amino acid production using a methanol-assimilating bacterium.

Hereinafter, the present invention will be explained in detail.

DNA of the Present Invention

The DNA of the present invention is a DNA that promotes secretion of L-lysine, L-arginine or both to the outside of a cell when it is introduced into a methanol-assimilating bacterium, and it is a DNA that encodes a variant of a protein which is involved in the secretion of L-lysine to the outside of a cell of the microorganism.

In the present invention, the expression "facilitating secretion of L-lysine, L-arginine or both to the outside of a cell" means that when a methanol-assimilating bacterium containing the DNA of the present invention is cultured in a medium, it provides an increased amount of L-lysine, L-arginine or both secreted into the medium compared with the methanol-assimilating bacterium not containing the DNA of the present invention. The increased secretion of the L-amino acids from the inside to the outside of the cell is demonstrated by increasing L-amino acid accumulation in the medium during the culture of the methanol-assimilating bacterium containing the DNA of the present invention as compared with the accumulation observed when culturing the methanol-assimilating bacterium not containing the DNA of the present invention. Furthermore, the increased secretion of the L-amino acids to the outside of a cell may also be observed as decreasing intracellular concentrations of the L-amino acids when the DNA of the present invention is introduced into a methanol-assimilating bacterium.

The *Methylobacillus* bacterium of the present invention is a bacterium which belongs to the genus *Methylobacillus* and can grow using methanol as a main carbon source, and in which secretion of an L-amino acid such as L-lysine or L-arginine is facilitated by introducing the DNA of the present invention. Specific examples thereof include, but are not limited to *Methylobacillus glycogenes*, *Methylobacillus flagellatum* and so forth. Examples of *Methylobacillus glycogenes* include, but are not limited to the T-11 strain (NCIMB 11375), ATCC 21276 strain, ATCC 21371 strain, ATR80 strain (see Appl. Microbiol. Biotechnol., 42, 67-72 (1994)), A513 strain (see Appl. Microbiol. Biotechnol., 42, 67-72 (1994)) and so forth. The *Methylobacillus glycogenes* NCIMB 11375 strain is available from the National Collections of Industrial and Marine Bacteria (NCIMB Lts., Torry Research Station, 135, Abbey Road, Aberdeen AB9 8DG, United Kingdom). Examples of *Methylobacillus flagellatum* include, but are not limited to the KT strain (see Arch. Microbiol., 149, 441-446 (1988)) and so forth.

The *Methylobacillus* bacterium of the present invention can be obtained by introducing a DNA encoding a variant of a protein having a loop region and six hydrophobic helixes which is involved in secretion of L-lysine to the outside of a cell, whereby the DNA has a mutation which results in deletion of the loop region, and/or results in the protein variant substantially consisting of only the hydrophobic helices. The expression "substantially consisting of only the hydrophobic helixes" means that the mutant LysE is completely deficient in the loop region or deficient in most of the loop region to such an extent that the function of the mutant LysE should not be affected.

One of the embodiments of the *Methylobacillus* bacterium of the present invention is a *Methylobacillus* bacterium into which the DNA designated as lysE24 described in the examples has been introduced. The gene lysE24 is a mutant gene isolated from *Brevibacterium lactofermentum* 2256 strain, and is a homologue of the known lysE gene from *Corynebacterium glutamicum* R127 strain. Therefore, the DNA which is introduced into the *Methylobacillus* bacterium of the present invention may also be referred to as a "mutant lysE" for convenience.

The LysE protein that is encoded by the lysE gene has six hydrophobic helix regions. Some of these hydrophobic regions are estimated to be transmembrane domains. It is also estimated that a region between the third and fourth regions from the N-terminus is hydrophilic and has a loop structure. In the present invention, this hydrophilic region is called a loop region. The nucleotide sequence of wild-type lysE and the amino acid sequence of the LysE protein derived from *Brevibacterium lactofermentum* 2256 strain are shown in SEQ ID NOS: 7 and 8, respectively. In this amino acid sequence, the hydrophobic helix regions correspond to the amino acid numbers 5-20, 37-58, 67-93, 146-168, 181-203 and 211-232. The loop region corresponds to the amino acid numbers 94-145.

The inventors of the present invention found that the lysE gene was lethal in a methanol-assimilating bacterium, but that a DNA encoding a variant of the LysE protein that did not have the loop region or substantially consisted of only the hydrophobic helices, increased the secretion of L-lysine and/or L-arginine to the outside of a cell of methanol-assimilating bacterium. The DNA of the present invention encodes such a mutant LysE protein that does not have the aforementioned loop region, or that substantially consists of only the hydrophobic helices.

The aforementioned mutant LysE is not particularly limited so long as it has one or more hydrophobic helices and when expressed results in increased secretion of L-lysine, L-arginine or both when it is introduced into a methanol-assimilating bacterium. Specifically, a DNA encoding a mutant LysE that has all of the first to sixth hydrophobic helices from the N-terminus is encompassed. More specifically, a DNA encoding a peptide containing the first to third hydrophobic helices relative to the N-terminus, and encoding a peptide containing the fourth to sixth hydrophobic helices relative to the N-terminus is encompassed. The aforementioned lysE24 is an example of the mutant lysE that encodes a peptide containing the first to third hydrophobic helices and a peptide containing the fourth to sixth hydrophobic helices. The lysE24 gene is introduced by a mutation with a stop codon downstream from the region encoding the third hydrophobic helix. When a region downstream from this stop codon was deleted as described in the examples, the mutant lysE24 gene did not cause L-lysine to accumulate in the medium when expressed in *Methylobacillus glycogenes* NCIMB 11375 strain. Therefore, it is estimated that a peptide containing the first to third hydrophobic helices and a peptide containing the fourth to sixth hydrophobic helices are separately translated and function in *Methylobacillus*

*glycogenes*. The results show that introduction of the lysE24 gene into a *Methylobacillus* bacterium will result in improvement of the production of L-lysine or L-arginine.

Any microorganism can be used to generate a DNA encoding a protein involved in secretion of L-lysine to the outside of a cell, i.e., the lysE gene or its homologous gene, so long as it has a variant of the gene that can express the L-lysine secretion activity in a methanol-assimilating bacterium. Specifically, coryneform bacteria such as *Corynebacterium glutamicum* (*Brevibacterium lactofermentum*), *Escherichia* bacteria such as *Escherichia coli*, *Pseudomonas* bacteria such as *Pseudomonas aeruginosa*, *Mycobacterium* bacteria such as *Mycobacterium tuberculosis* and so forth are emcompassed.

Examples of the homologous gene of lysE include a DNA coding for a protein which is hybridizable under stringent conditions with a probe having the nucleotide sequence of SEQ ID NO: 7 or a part thereof, and encodes a protein exhibiting the function of the LysE protein in a methanol-assimilating bacterium as a result of the aforementioned amino acid substitution. The aforementioned "stringent conditions" include conditions under which a so-called specific hybrid is formed, and a non-specific hybrid is not formed. It is difficult to clearly express this condition by using any numerical value. However, for example, the stringent conditions include a condition under which DNAs having high homology, for example, DNAs having homology of 80% or more, preferably 90% or more, more preferably 95% or more, are hybridized with each other, whereas DNAs having homology lower than the above do not hybridize with each other. Alternatively, stringent conditions are exemplified by conditions whereby DNAs hybridize with each other at a salt concentration upon ordinary conditions of washing in Southern hybridization, i.e., 1×SSC, 0.1% SDS, preferably 0.1× SSC, 0.1% SDS, at 60° C.

A partial sequence of the nucleotide sequence of SEQ ID NO: 7 can also be used as the probe. Such a probe can be prepared by PCR using oligonucleotides based on the nucleotide sequence of SEQ ID NO: 7 as primers and a DNA fragment containing the nucleotide sequence of SEQ ID NO: 7 as a template. When a DNA fragment having a length of about 300 bp is used as the probe, the washing conditions of hybridization can be, for example, 2×SSC, 0.1% SDS at 50° C.

In order to enhance the amino acid secretion gene expression in a *Methylophilus* bacterium, the gene fragment containing a lysE gene is ligated to a vector which is able to function in the *Methylophilus* bacterium, preferably a multi-copy type vector, to prepare a recombinant DNA which is then used to transform a host such as a *Methylophilus* bacterium. Alternatively, the gene can be incorporated into a transposon and introduced into the chromosome. Furthermore, a promoter that induces potent transcription in a *Methylophilus* bacterium can be ligated upstream from the gene.

The reference WO97/23597 discloses lysE, and only shows the lysE gene of coryneform bacterium introduced into a coryneform bacterium. Furthermore, it only mentions L-lysine as the secreted amino acid, and discloses a novel protein secretion system, including LysE having a structure containing six transmembrane helices. However, the inventors of the present invention confirmed that LysE derived from coryneform bacteria did not function at all in methanol-assimilating bacteria.

Furthermore, the obtained factor is a novel L-lysine secretion factor, which has a basic structure different from the known LysE of coryneform bacteria havine six transmembrane helices on one polypeptide, and this factor can no way be anticipated from the disclosure of the aforementioned patent specification that discloses LysE.

*Methylobacillus* Bacterium of the Present Invention

The *Methylobacillus* bacterium of the present invention is introduced with the DNA of the present invention which is able to be expressed, and has an ability to produce L-lysine or L-arginine. It can be obtained by introducing the DNA of the present invention into a *Methylobacillus* bacterium that has the L-lysine or L-arginine producing ability. The *Methylobacillus* bacterium of the present invention can also be obtained by imparting a L-lysine or L-arginine producing ability to a *Methylobacillus* bacterium introduced with the DNA of the present invention. The *Methylobacillus* bacterium of the present invention may also be obtained by imparting a L-lysine or L-arginine producing ability by introduction of the DNA of the present invention which is able to be expressed.

A Methylobacillus bacterium having the L-lysine or L-arginine producing ability can be obtained by imparting a L-lysine or L-arginine producing ability to a wild-type strain of a *Methylobacillus* bacterium. Methods conventionally used for breeding of coryneform bacteria, *Escherichia* bacteria, and so forth can be used to impart the L-lysine or L-arginine producing ability. For example, such methods include, but are not limited to acquisition of auxotrophic mutant strains, analogue resistant strains or metabolic regulation mutant strains, creation of recombinant strains in which an L-lysine or L-arginine biosynthesis system enzyme is enhanced (see "Amino Acid Fermentation", the Japan Scientific Societies Press [Gakkai Shuppan Center], 1 st Edition, published on May 30, 1986, pp. 77 to 100) and so forth. Properties of auxotrophy, analogue resistance, metabolic regulation mutation and so forth may be individually imparted or two or more may be imparted in combination when breeding L-lysine or L-arginine producing bacteria. The biosynthesis system enzyme may be individually enhanced or two or more of them may be enhanced in combination. Furthermore, the impartation of the properties including auxotrophy, analogue resistance, metabolic regulation mutation and so forth may be combined with the enhancement of biosynthesis system enzyme.

For example, L-lysine producing bacteria can be bred to be auxotrophic for L-homoserine or L-threonine and L-methionine (Japanese Patent Publication Nos. 48-28078 and 56-6499), or be auxotrophic for inositol or acetic acid (Japanese Patent Laid-open Nos. 55-9784 and 56-8692), or be resistant to oxalysine, lysine hydroxamate, S-(2-aminoethyl)-cysteine, γ-methyllysine, α-chlorocaprolactam, DL-α-amino-ε-caprolactam, α-amino-lauryllactam, aspartic acid analogue, sulfa drug, quinoid or N-lauroylleucine.

L-arginine producing bacteria can be bred to be resistant to a certain agent, for example, sulfa drug, 2-thiazolealanine, α-amino-β-hydroxyvaleric acid or the like; to be auxotrophic for L-histidine, L-proline, L-threonine, L-isoleucine, L-methionine or L-tryptophan in addition to resistance to 2-thiazolealanine (Japanese Patent Laid-open No. 54-44096); to be resistant to ketomalonic acid, fluoromalonic acid or monofluoroacetic acid (Japanese Patent Laid-open No. 57-18989); to be resistant to argininol (Japanese Patent Laid-open No. 62-24075); to be resistant to X-guanidine (X represents a derivative of fatty acid or aliphatic chain, Japanese Patent Laid-open No. 2-186995); to be resistant to 5-azauracil, 6-azauracil, 2-thiouracil, 5-fluorouracil, 5-bromouracil, 5-azacytosine, 6-azacytosine and so forth; to be resistant to arginine hydroxamate and 2-thiouracil; to be resistant to arginine hydroxamate and 6-azauracil (see Japanese Patent Laid-open No. 57-150381); to be resistant to a histidine analogue or tryptophan analogue (see Japanese Patent Laid-open No. 52-114092); to be auxotrophic for at least one of methionine, histidine, threonine, proline, isoleucine, lysine, adenine, guanine and uracil (or uracil precursor) (see Japanese Patent Laid-open No. 52-99289); to be resistant to arginine hydroxamate (see Japanese Patent Publication No. 51-6754); to be auxotrophic for succinic acid or resistant to a nucleic acid base analogue (Japanese Patent Laid-open No. 58-9692); to be deficient in the ability to metabolize arginine and to be resistant to an arginine antagonist and canavanine and auxotorophic for lysine (see Japanese Patent Laid-open No. 52-8729); to be resistant to arginine, arginine hydroxamate, homoarginine, D-arginine and canavanine, or resistant to arginine hydroxamate and 6-azauracil (see Japanese Patent Laid-open No. 53-143288); to be resistant to canavanine (see Japanese Patent Laid-open No. 53-3586) and so forth.

Hereinafter, methods for imparting or enhancing L-amino acid producing ability by enhancing an L-amino acid biosynthetic enzyme gene are exemplified.

L-lysine producing ability can be imparted by, for example, enhancing the activities of dihydrodipicolinate synthase and aspartokinase. The activities of dihydrodipicolinate synthase and aspartokinase in a *Methylophilus* bacterium can be enhanced by transforming a host such as *Methylophilus* bacterium with a recombinant DNA prepared by ligating a gene fragment encoding dihydrodipicolinate synthase and a gene fragment encoding aspartokinase with a vector that functions in the *Methylophilus* bacterium, preferably a multiple copy type vector. The increase in copy numbers of the genes encoding dihydrodipicolinate synthase and aspartokinase in the transformant strain results in an enhancement in the activities of these enzymes. Hereinafter, dihydrodipicolinate synthase, aspartokinase and aspartokinase III are also referred to as DDPS, AK and AKIII, respectively.

Any microorganism may provide the genes which encode DDPS and AK, so long as the chosen microorganism can express DDPS and AK activity in a *Methylobacillus*. Such microorganisms may be wild-type strains, or mutant strains derived therefrom. Specifically, examples of such microorganisms include *E. coli* (*Escherichia coli*) K-12 strain, *Methylobacillus glycogenes* NCIMB 11375 and so forth. Since nucleotide sequences for the genes encoding DDPS (dapA, Richaud, F. et al., J. Bacteriol., 297 (1986)) and AKIII (lysC, Cassan, M., Parsot, C., Cohen, G. N. and Patte, J. C., J. Biol. Chem., 261, 1052 (1986)) are known, these genes can be obtained by PCR using primers synthesized based on the nucleotide sequences of these genes, and using chromosomal DNA of microorganism such as *E. coli* K-12 as a template. Specific examples include, but are not limited to dapA and lysC derived from *E. coli*, as explained herein.

Preferably, the DDPS and AK used for the present invention will not be subject to feedback inhibition by L-lysine. It is known that wild-type DDPS derived from *E. coli* is subject to feedback inhibition by L-lysine (see U.S. Pat. Nos. 5,661,012 and 6,040,160), and that wild-type AKIII derived from *E. coli* is subject to suppression and feedback inhibition by L-lysine. Therefore, dapA and lysC preferably encode for DDPS and AKIII, respectively, each of which contain a mutation that eliminates the feedback inhibition by L-lysine upon introduction into a *Methylophilus* bacterium. Hereinafter, DDPS which contains a mutation that eliminates the feedback inhibition by L-lysine may also be referred to as "mutant DDPS," and a DNA encoding the mutant DDPS may also be referred to as "mutant dapA," or "dapA*." AKIII derived from *E. coli* which contains a mutation that eliminates the feedback inhibition by L-lysine may also be referred to as "mutant AKIII," and a DNA encoding the mutant AKIII may also be referred to as "mutant lysC".

However, it is not always necessary that DDPS and AK be mutated in the present invention. It is known that, for example, DDPS derived from *Corynebacterium* does not suffer feedback inhibition by L-lysine (see Korean Patent Publication No. 92-8382, U.S. Pat. Nos. 5,661,012 and 6,040,160).

A nucleotide sequence of wild-type dapA derived from *E. coli* is exemplified in SEQ ID NO: 13, and the amino acid sequence of wild-type DDPS encoded by the nucleotide sequence is exemplified in SEQ ID NO: 14.

The DNA encoding mutant DDPS that does not suffer feedback inhibition by L-lysine may be a DNA encoding DDPS having the amino acid sequence including replacing the histidine residue at position 118 with a tyrosine residue. Furthermore, the DNA encoding mutant AKIII that does not suffer feedback inhibition by L-lysine may be a DNA encoding AKIII having the amino acid sequence including replacing the threonine residue at position 352 with an isoleucine residue (see U.S. Pat. Nos. 5,661,012 and 6,040,160).

The plasmid used for gene cloning may be any plasmid so long as it can replicate in microorganisms such as *Escherichia* bacteria. Specifically, examples of such plasmids include pBR322, pTWV228, pMW119, pUC19 and so forth.

Vectors that function in *Methylobacillus* bacteria include, for example, a plasmid that can autonomously replicate in *Methylobacillus* bacteria. Specifically, examples include RSF1010, which is a broad host spectrum vector, and derivatives thereof, for example, pAYC32 (Chistorerdov, A. Y., Tsygankov, Y. D. Plasmid, 16, 161-167 (1986)), pMFY42 (Gene, 44, 53 (1990)), pRP301, pTB70 (Nature, 287, 396, (1980)) and so forth.

To prepare a recombinant DNA via ligation of dapA and lysC to a vector that functions in *Methylobacillus* bacteria, the vector is digested with a restriction enzyme suitable for the terminus of a DNA fragment containing dapa and lysC. The ligation is usually performed by using a ligase such as T4 DNA ligase. The genes dapa and lysC may be individually incorporated into separate vectors or the same vector.

A broad host spectrum plasmid RSFD80 is known (WO95/16042), and may be used in the present invention as the plasmid having a mutant dapa encoding a mutant DDPS and mutant lysC encoding a mutant AKIII. An *E. coli* JM109 strain transformed with this plasmid was designated as AJ12396, and deposited at the National Institute of Bioscience and Human-Technology, Agency of Industrial Science and Technology, Ministry of International Trade and Industry (currently, the independent administrative corporation, National Institute of Advanced Industrial Science and Technology, International Patent Organism Depositary) on Oct. 28, 1993 and received an accession number of FERM P-13936. Then, the deposit was converted to an international deposit under the provisions of the Budapest Treaty on Nov. 1, 1994, and received an accession number of FERM BP-4859. RSFD80 can be obtained from the AJ12396 strain by a known method.

Any method can be used to introduce a recombinant DNA prepared as described above into a *Methylophilus* bacterium, so long as it provides sufficient transformation efficiency. For example, electroporation can be used (Canadian Journal of Microbiology, 43, 197 (1997)).

The DDPS and AK activities can also be enhanced by the presence of multiple copies of dapA and lysC on chromosomal DNA of a *Methylobacillus* bacterium. Multiple copies of dapa and lysC may be introduced into the chromosomal DNA of a *Methylobacillus* bacterium by homologous recombination. This can be performed by targeting a sequence present on chromosomal DNA in multiple copy number. A repetitive DNA or an inverted repeat present at the end of a transposable element can be used as the sequence present on the chromosomal DNA in a multiple copy number. Alternatively, as disclosed in Japanese Patent Laid-open No. 2-109985, multiple copies of dapA and/or lysC can be introduced into the chromosomal DNA by incorporating them into a transposon and transferring it. In both of the methods, activities of DDPS and AK will be amplified as a result of increased copy numbers of dapA and lysC in transformant strains.

Besides the above gene amplification methods, the DDPS activity and AK activity can be amplified by replacing expression control sequences, such as promoters of dapa and lysC, with stronger ones (see Japanese Patent Laid-open No. 1-215280). Examples of such strong promoters are known, and include, for example, lac promoter, trp promoter, trc promoter, tac promoter, $P_R$ promoter and $P_L$ promoter of lambda phage, tet promoter, amyE promoter, spac promoter and so forth. Use of these strong promoters enhances expression of dapa and lysC, and thus DDPS activity and AK activity will be amplified. Such gene expression enhancement methods can be combined with the with the gene amplification (increasing the copy number of dapA and lysC) methods described above.

Preparation of a recombinant DNA can be accomplished by ligating a gene fragment and a vector once the vector is digested with a restriction enzyme corresponding to the terminus of the gene fragment. Ligation is usually performed by ligase such as T4 DNA ligase. The usual methods well known to those with skill in the art can be used as methods for digestion, ligation of DNA, preparation of chromosomal DNA, PCR, preparation of plasmid DNA, transformation, design of oligonucleotides used as primers and so forth. Such methods are described in Sambrook, J., Fritsch, E. F., and Maniatis, T., "Molecular Cloning A Laboratory Manual, Second Edition", Cold Spring Harbor Laboratory Press (1989) and so forth.

In addition to the enhancement of DDPS and AK gene expression or activity, other enzymes involved in the L-lysine biosynthesis may also be enhanced. Such enzymes include diaminopimelate pathway enzymes such as dihydrodipicolinate reductase, diaminopimelate decarboxylase, diaminopimelate dehydrogenase (see WO96/40934 for all of the foregoing enzymes), phosphoenolpyruvate carboxylase (Japanese Patent Laid-open No. 60-87788), aspartate aminotransferase (Japanese Patent Publication No. 6-102028), diaminopimelate epimerase and aspartate semialdehyde dehydrogenase, aminoadipate pathway enzymes such as homoaconitate hydratase and so forth.

Aspartokinase, aspartate semialdehyde dehydrogenase, dihydrodipicolinate synthase, dihydrodipicolinate reductase and diaminopimelate decarboxylase derived from *Methylophilus methylotrophus* as a methanol-assimilating bacterium are disclosed in WO 00/61723.

Furthermore, the microorganisms of the present invention may have decreased activity of an enzyme that catalyzes a reaction for generating a compound other than L-lysine by branching off from the biosynthetic pathway for L-lysine, or may be deficient in such an enzyme. Illustrative examples of the enzyme that catalyzes a reaction for generating a compound other than L-lysine by branching off from the biosynthetic pathway for L-lysine include homoserine dehydrogenase (see WO95/23864).

The aforementioned techniques for enhancing activities of enzymes involved in the L-lysine biosynthesis can be similarly used for L-arginine.

L-arginine producing ability can be improved by enhancing acetylornithine deacetylase activity, N-acetylglutamate-γ-semialdehyde dehydrogenase activity, N-acetyl glutamokinase activity and argininosuccinase activity (Japanese Patent Publication No. 5-23750).

L-arginine producing ability can also be improved by enhancing activity of glutamate dehydrogenase (EP 1 057 893 A1), argininosuccinate synthase (EPO 999 267 A1), carbamoyl phosphate synthetase (EPI 026 247 A1) or N-acetylglutamate synthase (see Japanese Patent Laid-open No. 57-5693) or by disrupting the gene encoding an arginine repressor (argR).

Production of L-Lysine or L-Arginine

L-lysine or L-arginine can be produced by culturing a *Mehylobaccilus* bacterium having L-lysine or L-arginine producing ability. L-lysine or L-arginine can be obtained as described above from a medium upon production and accumulation. L-lysine or L-arginine can then be collected from the culture.

The microorganism used for the present invention can be cultured by a method typically used in culture of a methanol-assimilating microorganism. The medium used for the present invention may be either a natural or synthetic medium so long as it contains a carbon source, nitrogen source, inorganic ions and other trace amount organic components as required.

If methanol is used as a main carbon source, L-lysine or L-arginine can be produced at a low cost. When methanol is used as a main carbon source, it is added to a medium in an amount of between 0.001 to 30%. As the nitrogen source, ammonium sulfate or the like is used by adding it to the medium. In addition to these, trace amount components such as potassium phosphate, sodium phosphate, magnesium sulfate, ferrous sulfate, manganese sulfate and so forth, can be added in small amounts.

The culture is usually performed under aerobic conditions by shaking, or aeration by stirring, or the like at a pH of between 5 to 9, and a temperature of between 20 to 45° C., and it is typically complete within 24 to 120 hours.

Collection of L-lysine or L-arginine can usually be collected from culture by a combination of ion exchange resin method, precipitation method, and other known methods.

EXAMPLES

Hereafter, the present invention will be explained more specifically with reference to the following examples.

The reagents used in the following examples were obtained from Wako Pure Chemicals or Nacalai Tesque, unless otherwise indicated. The compositions of the media used in each example are shown below. pH was adjusted with NaOH or HCl for all of the media.

LB Medium:

| | |
|---|---|
| Trypton peptone (Difco) | 10 g/L |
| Yeast extract (Difco) | 5 g/L |
| NaCl | 10 g/L |
| pH 7.0 | |

These were steam-sterilized at 120° C. for 20 minutes.

LB Agar Medium:

| LB medium | |
|---|---|
| Bacto agar | 15 g/L |

These were steam-sterilized at 120° C. for 20 minutes.

SEII medium (see Journal of General Microbiology (1989) 125, 135, 3153-3164, Silman N. J., Carver M. A. & Jones C. W.; A part of the composition was modified.):

| | |
|---|---|
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 µg/L |
| $MnSO_4 \cdot 5H_2O$ | 25 µg/L |
| $ZnSO_4 \cdot 7H_2O$ | 23 µg/L |
| $CaCl_2 \cdot 2H_2O$ | 72 µg/L |
| $FeCl_3 \cdot 6H_2O$ | 9.7 mg/L |
| $CaCO_3$(Kanto Kagaku) | 30 g/L |

-continued

| | |
|---|---|
| Methanol | 2% (vol/vol) |
| pH 7.0 | |

Except for methanol, the components were steam-sterilized at 121° C. for 15 minutes. After the components were sufficiently cooled, methanol was added.

SEII Agar Medium:

| | |
|---|---|
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 μg/L |
| $MnSO_4 \cdot 5H_2O$ | 25 μg/L |
| $ZnSO_4 \cdot 7H_2O$ | 23 μg/L |
| $CaCl_2 \cdot 2H_2O$ | 72 mg/L |
| $FeCl_3 \cdot 6H_2O$ | 9.7 mg/L |
| Methanol | 0.5% (vol/vol) |
| pH 7.0 | |
| Bacto agar (Difco) | 15 g/L |

Except for methanol, the components were steam-sterilized at 121° C. for 15 minutes. After the components were sufficiently cooled, methanol was added.

Example 1

Introduction of lysE Gene Derived from *Brevibacterium* Bacterium into *Methylophilus* Bacterium A lysE gene, which was a homologous gene of the gene facilitating secretion of L-lysine known for *Corynebacterium glutamicum* R127, was cloned from a *Brevibacterium lactofermentum* 2256 strain, and expression was attempted in a *Methylophilus* bacterium.

(1) Construction of pRSlysE

In order to introduce lysE into a *Methylophilus* bacterium, a known plasmid pRS (see International Patent Publication in Japanese (Kohyo) No. 3-501682) was used to construct a plasmid pRSlysE for expression of lysE. pRS is a plasmid having the vector segment of the pVIC40 plasmid (International Patent Publication WO90/04636, International Patent Publication in Japanese No. 3-501682) and obtained from pVIC40 by deleting a DNA region encoding the threonine operon contained in the plasmid. The plasmid pVIC40 is derived from a broad host spectrum vector plasmid pAYC32 (Chistorerdov, A. Y., Tsygankov, Y. D., Plasmid, 1986, 16, 161-167), which is a derivative of RSF1010.

First, a plasmid pRStac having the tac promoter was constructed from pRS according to the scheme shown in FIG. 1. The pRStac plasmid was constructed as follows. The pRS vector was digested with restriction enzymes EcoRI and PstI and added to a phenol/chloroform solution and mixed to terminate the reaction. After the reaction mixture was centrifuged, the upper layer was collected, and DNAs were collected by ethanol precipitation and separated on 0.8% agarose gel. A DNA fragment of 8 kilobase pairs (hereinafter, "kbp") was collected by using EASY TRAP Ver. 2 (DNA collection kit, Takara Shuzo). Alternatively, the tac promoter region was amplified by PCR using the pKK223-3 plasmid (expression vector, Pharmacia) as a template and the primers shown in SEQ ID NOS: 1 and 2 (a cycle consisting of denaturation at 94° C. for 20 seconds, annealing at 55° C. for 30 seconds and extension reaction at 72° C. for 60 seconds was repeated for 30 cycles). Pyrobest DNA polymerase (Takara Shuzo) was used for PCR. The DNA fragment containing the amplified tac promoter was purified by using PCR prep (Promega) and then digested at the restriction enzyme sites preliminarily designed in the primers, i.e., at EcoRI and EcoT22I sites. Then, the reaction mixture was added to a phenol/chloroform solution and mixed to terminate the reaction. After the reaction mixture was centrifuged, the upper layer was collected and DNAs were collected by ethanol precipitation and separated on 0.8% agarose gel. A DNA fragment of about 0.15 kbp was collected by using EASY TRAP Ver. 2.

The digestion product of the pRS vector and the tac promoter region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes to obtain pRStac. A plasmid in which the transcription directions of the streptomycin resistance gene on the pRS vector and the tac promoter were identical to each other was selected as pRStac.

pRStac obtained as described above was digested with Sse8387I (Takara Shuzo) and SapI (New England Biolabs), added to a phenol/chloroform solution and mixed to terminate the reaction. After the reaction mixture was centrifuged, the upper layer was collected and DNAs were collected by ethanol precipitation and separated on 0.8% agarose gel to obtain a DNA fragment of about 9.0 kbp.

The lysE gene fragment was also amplified by PCR using chromosome extracted from the *Brevibacterium lactofermentum* 2256 strain (ATCC13869) as a template and the primers shown in SEQ ID NOS: 5 and 6 (denaturation at 94° C. for 20 seconds, annealing at 55° C. for 30 seconds and extension reaction at 72° C. for 90 seconds). Pyrobest DNA polymerase (Takara Shuzo) was used for PCR. To enable expression of the lysE gene in a *Methylophilus* bacterium, the primers were designed so that nucleotides of 9-15 bp from the translation initiation codon of the lysE gene should be replaced with a sequence that is known to function in a *Methylophilus* bacterium (Wyborn, N. R., Mills, J., Williamis, S. G. and Jones, C. W., Eur. J. Biochem., 240, 314-322 (1996)). The resulting fragment was purified by using PCR prep (Promega) and then digested with Sse8387I and SapI. The reaction mixture was added to a phenol/chloroform solution and mixed to terminate the reaction. After the reaction mixture was centrifuged, the upper layer was collected and DNAs were collected by ethanol precipitation and further collected from 0.8% agarose gel.

The digestion product of the pRStac vector and the lysE gene region fragment prepared as described above were ligated using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence, confirming the presence of pRSlysE (FIG. 1). In pRSlysE, the lysE gene was positioned so that its transcription direction is the same as that of the tac promoter.

(2) Introduction of pRSlysE into *Methylophilus* Bacterium pRSlysE obtained as described above was introduced into *Methylophilus methylotrophus* AS1 strain (NCIMB 10515) by electroporation (Canadian Journal of Microbiology, 43, 197 (1997)). In addition, pRS was also introduced into the AS1 strain as a control in the same manner as for pRSlysE. As a result, several thousands of colonies were obtained per 1 μg of DNA with pRS used as a control, whereas only several colonies were obtained with pRSlysE.

When plasmids were extracted from transformant strains estimated to be introduced with pRSlysE and their nucleotide sequences investigated, a spontaneous mutation was introduced in a region encoding lysE for all the investigated plasmids, and in some cases, a nonsense mutation was introduced as the mutation, by which a codon encoding an amino acid was replaced with a stop codon that terminated the translation. In other plasmids, deletion was observed in the lysE gene. Iin either case, the function of lysE in pRSlysE was lost. However, when a plasmid was prepared in which a part of the region encoding lysE was intentionally deleted so that the function of the lysE gene is eliminated (pRSlysEΔ1) and introduced into *Methylophilus methylotrophus*, it could be introduced at a frequency equivalent to that of the control pRS vector.

The aforementioned pRSlysEΔ1 was a plasmid in which a region from PvuI site (recognizes CGATCG of the 203-209th positions in SEQ ID NO: 7) to MluI site (recognizes ACGCGT of the 485-491 st positions of the same) present in the region encoding lysE was deleted. Specifically, pRSlysE was constructed by digestion with PvuI and MluI (Takara Shuzo), added to a phenol/chloroform solution and mixed to terminate the reaction. After the reaction mixture was centrifuged, the upper layer was collected and DNAs were collected by ethanol precipitation and separated on 0.8% agarose gel to obtain a DNA fragment of about 10 kbp. This DNA fragment was blunt-ended by using DNA Blunting Kit (Takara Shuzo). The product was self-ligated using DNA Ligation Kit Ver. 2 (Takara Shuzo).

This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method, and the structure of each plasmid was confirmed by digestion with restriction enzymes, to obtain the pRSlysEΔ1 plasmid.

As described above, the introduction frequency of pRSlysE carrying the full length lysE gene into *Methylophilus methylotrophus* was extremely low, and only plasmids having a lysE mutant gene containing a mutation that eliminated the function could be introduced. Considering these facts together, it was estimated that the introduction of the lysE gene into *Methylophilus methylotrophus* was lethal. This indicates that the lysE gene cannot universally function for the secretion of L-lysine in heterogenous bacteria.

The *Methylophilus methylotrophus* AS1 strain harboring pRSlysE containing the above described mutation was applied to an SEII plate containing 20 mg/L of streptomycin and cultured overnight at 37° C. Then, the cells from about 0.3 cm² of the medium surface were scraped, inoculated into SEII production medium (20 ml) containing 20 mg/L of streptomycin, and cultured at 37° C. for 34 hours with shaking. After completion of the culture, the cells were removed by centrifugation and the L-lysine concentration in the culture supernatant was determined by using an amino acid analyzer (Nihon Bunko, high speed liquid chromatography). As a result, substantially no strain was obtained in which secretion of L-lysine was enhanced in spite of introduction of the mutant lysE gene.

Acquisition of Gene Providing L-Lysine Secretion Activity in *Methylophilus* Bacteria As described in the preceding section, the known lysE gene is lethal in *Methylophilus* bacteria, and as a result, many mutant genes for which function was lost were subsequently obtained.

During analysis of pRSlysE containing a mutation, a mutant lysE gene that functioned in *Methylophilus* bacteria but was not lethal was obtained.

This mutant lysE gene was designated as lysE24 gene. When the nucleotide sequence of lysE24 gene was analyzed, it was found that this mutation did not result in an amino acid substitution, but a nonsense mutation introducing a stop codon around the center of the translation region of lysE. It has been reported that the lysE gene of *Corynebacterium* bacteria encodes a membrane protein having six hydrophobic helices (Vrlijc M., Sahm H., and Eggeling L., Molecular Microbiology 22:815-826 (1996)). In contrast, it was found that since the above lysE24 gene contained a stop codon, the protein encoded by this gene had a structure different from that of the wild-type LysE protein. As a result, the LysE mutant functioned in *Methylophilus* bacteria due to this structure.

The nucleotide sequence of lysE24 and the amino acid sequence encoded by the nucleotide sequence are shown in SEQ ID NOS: 9 and 10, respectively. The nucleotide sequence of wild-type lysE and the amino acid sequence encoded by the nucleotide sequence are shown in SEQ IDS NO: 7 and 8, respectively. In lysE24, T (thymine) was inserted after G (guanine) at the 355th position of the wild-type lysE gene. The plasmid having lysE24 was designated as pRSlysE24 (FIG. 1). When pRSlysE24 was introduced anew into the AS 1 strain, the plasmid could be introduced at a frequency substantially equivalent to that of pRS. In Table 1, the result of L-lysine concentration measurement for culture supernatant of the plasmid-introduced strain is shown, which measurement was performed in the same manner as above (Example 1, part (2)).

TABLE 1

| Strain | Production amount of L-lysine (g/L) |
|---|---|
| AS1/pRS | <0.01 |
| AS1/pRSlysE24 | 0.1 |

The *E. coli* JM109 strain transformed with pRSlysE24 was designated as AJ13830, and this strain was deposited at the independent administrative corporation, National Institute of Advanced Industrial Science and Technology, International Patent Organism Depositary on Jun. 4, 2001 and received an accession number of FERM P-18369. Then, the deposit was converted to an international deposit under the provisions of the Budapest Treaty on May 13, 2002, and received an accession number of FERM BP-8040.

The AS1 strain containing a plasmid which was obtained from the lysE24 gene by deleting a region downstream from the stop codon generated by the aforementioned mutation, that is, the pRSlysEΔ1 plasmid described in Example 1, part (1), did not accumulate L-lysine in the medium. Based on this result, it is estimated that not only the first half of the peptide, but also the latter half of the peptide was expressed from the lysE24 gene to form a complex.

Example 2

As described above, it was found that the lysE gene, which is homologous to the gene that facilitates secretion of L-lysine for *Corynebacterium*, did not function in *Methylophilus* bacteria at all, whereas its variant lysE24 functioned in *Methylophilus* bacteria. Accordingly, whether lysE gene of a *Corynebacterium* and lysE24 obtained in Example 1 would function in a *Methylobacillus* bacterium were investigated.

(1) Construction of pRSlysE-Tc

In order to introduce wild-type lysE gene derived from a *Corynebacterium* into a *Methylobacillus* bacterium, the drug resistance marker of the pRSlysE constructed in Example 1 was first changed from a streptomycin resistance gene to a tetracycline resistance gene. This is because streptomycin resistance cannot be used as a marker since *Methylobacillus* bacteria originally exhibited resistance to streptomycin.

Specifically, pRSlysE was first digested with the restriction enzyme EcoRI, added to a phenol/chloroform solution and mixed to terminate the digestion reaction. After the reaction mixture was centrifuged, the upper layer solution was collected, and DNA fragments were collected by ethanol precipitation and separated by 0.8% agarose gel electrophoresis. A DNA fragment of about 10 kbp was collected by using EASY TRAP Ver. 2 (DNA Collection Kit, Takara Shuzo).

The tetracycline resistance gene region was amplified by PCR using pRK310 (Journal of Molecular Biology 239, 623-663 (1994)) as a template DNA and the DNA primers shown in SEQ ID NOS: 11 and 12 (a cycle consisting of denaturation at 94° C. for 20 seconds, annealing at 55° C. for 30 seconds and extension reaction at 72° C. for 60 seconds was repeated for 30 cycles). Pyrobest DNA polymerase (Takara Shuzo) was used for PCR. The DNA fragment containing the amplified tetracycline resistance gene was purified by using PCR prep (Promega) and then collected by ethanol precipitation. This fragment was further digested at the restriction sites preliminarily designed in the primers, i.e., digested at EcoRI site, and added to a phenol/chloroform solution and mixed to terminate the reaction. Subsequently, after this reaction mixture was centrifuged, the upper layer was collected, and DNAs were collected by ethanol precipitation. Then, the target DNA fragment was separated by 0.8% agarose gel electrophoresis to collect a DNA fragment of about 1.5 kbp.

The tetracycline resistance gene can also be obtained in the same manner as described above by PCR using another plasmid instead of pRK310, for example, the pRK2 plasmid, a parent plasmid of pRK310 (available as NICMB11968 from NICMB, see Science, 190, 1226-1228 (1975), or Plasmid, 5, 10-19 (1981)) as a template.

The DNA fragment derived from pRSlysE prepared as described above and the DNA fragment containing the tetracycline resistance gene region were ligated by using DNA Ligation Kit Ver. 2 (Takara Shuzo). This reaction mixture was used to transform *E. coli* JM109 competent cells (Takara Shuzo). The cells were plated on LB agar medium containing 20 mg/L of streptomycin and 15 mg/L of tetracycline and cultured overnight at 37° C. The colonies that appeared on the agar medium were each inoculated into LB liquid medium containing 20 mg/L of streptomycin and 15 mg/L of tetracycline and cultured at 37° C. for 8 hours with shaking. Plasmid DNA was extracted from this culture broth by the alkali-SDS method, and the structure of each plasmid was confirmed by digestion with restriction enzymes to obtain pRSlysE-Tc.

(2) Introduction of pRSlysE-Tc into *Methylobacillus* Bacterium pRSlysE-Tc obtained as described above was introduced into the *Methylobacillus glycogenes* NCIMB11375 strain by electroporation (Canadian Journal of Microbiology, 43, 197 (1997)). As a control, pRK310 was introduced into the NCIMB11375 strain in the same manner as that for pRSlysE-Tc. As a result, several thousands of colonies were obtained per 1 μg of DNA with pRK310 used as a control, whereas only several colonies were obtained with pRSlysE-Tc. Thus, it was found that the lysE gene derived from a *Corynebacterium* bacterium did not function in *Methylobacillus* bacteria as in *Methylophilus* bacteria.

(3) Construction of pRSlysE24-Tc

Subsequently, in order to investigate whether lysE24 functioned in *Methylobacillus* bacteria, the drug resistance marker of the pRSlysE24 plasmid constructed in Example 1 was changed from the streptomycin resistance gene to a tetracycline resistance gene.

Specifically, pRSlysE was first digested with a restriction enzyme EcoRI, added to a phenol/chloroform solution and mixed to terminate the digestion reaction. After the reaction mixture was centrifuged, the upper layer solution was collected, and DNA fragments were collected by ethanol precipitation and separated by 0.8% agarose gel electrophoresis. A DNA fragment of about 10 kbp was collected by using EASY TRAP Ver. 2 (DNA Collection Kit, Takara Shuzo).

Further, the tetracycline resistance gene fragment was obtained in the same manner as described above by amplifying the gene region from pRK310 by PCR using the primers shown in SEQ ID NOS: 11 and 12 and digesting the fragment with EcoRI.

The DNA fragment derived from pRSlysE24 prepared as described above and the DNA fragment containing the tetracycline resistance gene region were ligated by using DNA Ligation Kit Ver. 2 (Takara Shuzo). This reaction mixture was used to transform E. coli JM109 competent cells (Takara Shuzo). The cells were plated on LB agar medium containing 20 mg/L of streptomycin and 15 mg/L of tetracycline and cultured overnight at 37° C. The colonies that appeared on the agar medium were each inoculated into LB liquid medium containing 20 mg/L of streptomycin and 15 mg/L of tetracycline and cultured at 37° C. for 8 hours with shaking. Plasmid DNA was extracted from this culture broth by the alkali-SDS method, and the structure of each plasmid was confirmed by digestion with restriction enzymes, to obtain pRSlysE24-Tc.

(4) Introduction of pRSlysE24-Tc into *Methylobacillus* Bacterium pRSlysE24-Tc obtained as described above was introduced into the *Methylobacillus glycogenes* NCIMB11375 strain by electroporation (Canadian Journal of Microbiology, 43, 197 (1997)). In addition, pRK310 was introduced into the NCIMB11375 strain as a control. As a result, pRSlysE24-Tc could be introduced at a frequency substantially equivalent to that of the control pRK310. The results of L-lysine concentration measurement for culture supernatants of the plasmid-introduced strains are shown in Table 2, which measurement was performed in the same manner as in Example 1, part (2).

TABLE 2

| Strain | Production amount of L-lysine (g/L) | Production amount of L-arginine (g/L) |
|---|---|---|
| NCIMB11375/pRK310 | <0.01 | <0.01 |
| NCIMB11375/pRSlysE24-Tc | 1.57 | 0.16 |

It was found that introduction of the lysE24 gene into *Methylobacillus glycogenes* NICMB11375 strain resulted in accumulation of L-lysine in the medium. It was determined that this was caused by enhancement of the secretion of L-lysine. Furthermore, when concentrations of other L-amino acids in the culture supernatant were investigated, L-arginine was accumulated with the NCIMB11375/pRSlysE24-Tc strain, and thus it was found that lysE24 had activity for secreting not only L-lysine but also L-arginine.

From the above investigation, it was found that lysE24 which functioned in *Methylophilus* bacteria also functioned in *Methylobacillus* bacteria.

Example 3

Introduction of L-Lysine Biosynthesis System Enzyme Gene and lysE24 Gene into *Methylobacillus glycogenes*

It was found that when the lysE24 gene was introduced into *Methylobacillus glycogenes* NCIMB11375 strain, L-lysine accumulated in the medium. It was considered that this was caused by enhancement of the secretion of L-lysine. Therefore, the effect of introducing the lysE24 gene into *Methylobacillus glycogenes* on enhancement of the L-lysine biosynthesis gene was investigated.

<1> Construction of Plasmid pRSdapA Having dapA* Gene

A plasmid was prepared having a gene encoding dihydrodipicolinate synthase as an L-lysine biosynthesis system enzyme gene, that was not subject to feedback inhibition by L-lysine (dapA*).

pRStac prepared in Example 1 was digested with Sse8387I and XbaI and added to a phenol/chloroform solution and mixed to terminate the reaction. After the reaction mixture was centrifuged, the upper layer was collected, and DNAs were collected by ethanol precipitation and separated on 0.8% agarose gel to collect a DNA fragment of about 9 kbp.

The dapa* gene fragment was amplified by PCR using the known plasmid RSFD80 (see WO90/16042) which contains that gene as a template and the primers shown in SEQ ID NOS: 3 and 4 (denaturation at 94° C. for 20 seconds, annealing at 55° C. for 30 seconds and extension reaction at 72° C. for 60 seconds). Pyrobest DNA polymerase (Takara Shuzo) was used for PCR. The resulting dapa* fragment was purified using PCR prep (Promega) and then digested with restriction enzymes Sse8387I and XbaI. The reaction mixture was added to a phenol/chloroform solution and mixed to terminate the reaction. After the reaction mixture was centrifuged, the upper layer was collected and DNAs were collected by ethanol precipitation and separated on 0.8% agarose gel to collect a DAN fragment of about 0.1 kbp.

The digestion product of the pRStac vector and the dapa* gene region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and the structure of each plasmid was confirmed by digestion with restriction enzymes and determination of nucleotide sequence, confirming the presence of pRSdapA plasmid. In pRSdapA plasmid, the dapa* gene was positioned so that its transcription direction is the same as that of the tac promoter.

The *E. coli* JM109 strain transformed with the pRSdapA plasmid was designated as AJ13831, and this strain was deposited at the independent administrative corporation, National Institute of Advanced Industrial Science and Technology, International Patent Organism Depositary on Jun. 4, 2001 and received an accession number of FERM P-18370. Then, the deposit was converted to an international deposit under the provisions of the Budapest Treaty on May 13, 2002, and received an accession number of FERM BP-8041.

<2> Construction of Plasmid Having lysE24 and dapA*, SlysE24-dapA-Tc

Figure 2:
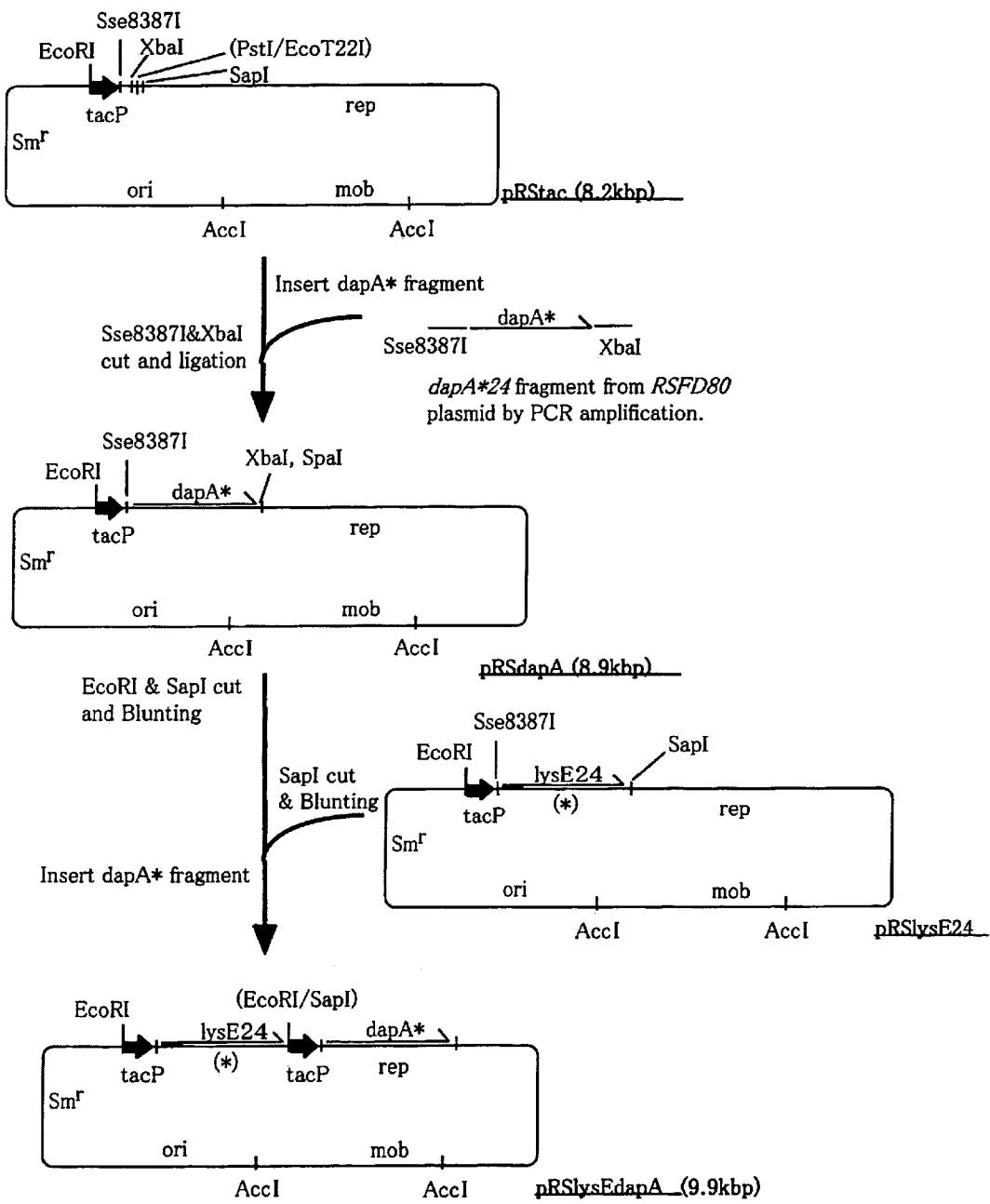
FIG. 2 shows construction of a plasmid pRSlysEdapA having the lysE24 gene and dapA* gene.

A plasmid having pRSlysE24 inserted with the dapA* gene was constructed according to the scheme shown in FIG. 2 to evaluate the effect of combining lysE24 and dapA*.

pRSlysE24 prepared in Example 1 was digested with a restriction enzyme SapI and blunt-ended by using DNA Blunting Kit (Takara Shuzo). The plasmid pRSdapA having dapA* was digested with restriction enzymes EcoRI and SapI, and a fragment of about 1 kbp containing tac promoter and dapA* region was separated on 0.8% agarose gel. This fragment was collected by using EASY TRAP Ver. 2 (Takara Shuzo). This fragment was blunt-ended as described above and ligated to the aforementioned digestion product of pRSlysE24 by using DNA Ligation Kit Ver. 2 (Takara Shuzo).

The aforementioned ligation reaction solution was used to transform Escherichia coli (E. coli JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from this culture broth by the alkali-SDS method, and the structure of each plasmid was confirmed by digestion with restriction enzymes and determination of nucleotide sequence, confirming the presence of the pRSlysEdapA plasmid.

The E. coli JM109 strain transformed with the pRSlysEdapA plasmid was designated as AJ13832, and this strain was deposited at the independent administrative corporation, National Institute of Advanced Industrial Science and Technology, International Patent Organism Depositary on Jun. 4, 2001 and received an accession number of FERM P-18371. Then, the deposit was converted to an international deposition under the provisions of the Budapest Treaty on May 13, 2002, and received an accession number of FERM BP-8042.

Subsequently, the drug resistance marker gene of the pRSlysEdapA plasmid was changed from a streptomycin resistance gene to a tetracycline resistance gene. First, the pRSlysEdapA plasmid was digested with a restriction enzyme EcoRI, added to a phenol/chloroform solution and mixed to terminate the digestion reaction. After the reaction mixture was centrifuged, the upper layer solution was collected, and DNA fragments were collected by ethanol precipitation and separated by 0.8% agarose gel electrophoresis. A DNA fragment of about 11 kbp was collected by using EASY TRAP Ver. 2 (DNA Collection Kit, Takara Shuzo).

The tetracycline resistance gene fragment was obtained in the same manner as in Example 1 by amplifying the gene region from pRK310 by PCR using the primers shown in SEQ ID NOS: 11 and 12 and digesting the amplification product with EcOR1.

The DNA fragment derived from pRSlysEdapA prepared as described above and the DNA fragment containing the tetracycline resistance gene region were ligated by using DNA Ligation Kit Ver. 0.2 (Takara Shuzo). This reaction mixture was used to transform E. coli JM109 competent cells (Takara Shuzo). The cells were plated on LB agar medium containing 20 mg/L of streptomycin and 15 mg/L of tetracycline and cultured overnight at 37° C. The colonies that appeared on the agar medium were each inoculated into LB liquid medium containing 20 mg/L of streptomycin and 15 mg/L of tetracycline and cultured at 37° C. for 16 hours with shaking. Plasmid DNA was extracted from this culture broth by the alkali-SDS method, and the structure of each plasmid was confirmed by digestion with restriction enzymes confirming the presence of pRSlysE-dapA-Tc.

(2) Introduction of pRSlysE-dapA-Tc into Methylobacillus Glycogenes NCIMB111375 Strain and Production of Amino Acids The pRSlysE-dapA-Tc plasmid obtained by the above method was introduced into the Methylobacillus glycogenes NCIMB111375 strain by electroporation. The obtained transformant strain (henceforth also referred to as "NCIMB111375/pRSlysE-dapA-Tc"), strain introduced with the aforementioned pRSlysE24-Tc (henceforth also referred to as "NCIMB111375/pRSlysE-Tc") and strain introduced with pRK310 as a control (henceforth also referred to as "NCIMB 111375/pRK310") were cultured as follows to investigate the L-amino acid concentrations in the culture supernatant.

Each transformant strain was applied to an SEII plate containing 15 mg/L of tetracycline and cultured at 30° C. for two days. Then, the cells on about 10 cm$^2$ of the medium surface were scraped, inoculated into SEII production medium (20 ml) containing 15 mg/L of tetracycline, and cultured at 37° C. for 60 hours with shaking. After completion of the culture, the cells were removed by centrifugation, and the L-lysine concentration in the culture supernatant was determined by using an amino acid analyzer (Nihon Bunko, high speed liquid chromatography). The results are shown in Table 3. It was found that the amount of L-lysine that accumulated in the medium further improved in the NCIMB/pRSlysE-dapA-Tc strain compared with the strain having pRSlysE24-Tc. That is, it is considered that the rate limitation regarding the secretion was cancelled by the introduction of the lysE24 gene, and the dapA* gene-enhancing effect was exhibited in a synergistic manner.

TABLE 3

| Strain | Production amount of L-lysine (g/L) | Production amount of L-arginine (g/L) |
| --- | --- | --- |
| NCIMB11375/pRK310 | <0.02 | <0.01 |
| NCIMB11375/pRSlysE24-Tc | 1.57 | 0.16 |
| NCIMB11375/pRSlysE-dapA-Tc | 1.72 | 0.14 |

While the invention has been described in detail with reference to preferred embodiments thereof, it will be apparent to one skilled in the art that various changes can be made, and equivalents employed, without departing from the scope of the invention. Each of the aforementioned documents, as well as the foreign priority document, JP2002336340, is incorporated by reference herein in its entirety.

What is claimed is:

1. A bacterium belonging to the genus *Methylobacillus*, into which a DNA which is able to be expressed is introduced, and which has an ability to produce L-lysine or L-arginine, wherein said DNA encodes a protein comprising the amino acid sequence of SEQ ID NO: 10.

2. A method for producing L-lysine or L-arginine, comprising culturing the bacterium belonging to the genus *Methylobacillus* of claim 1 in a medium to produce and accumulate L-lysine or L-arginine in culture, and collecting L-lysine or L-arginine from the culture.

3. The method for producing L-lysine or L-arginine according to claim 2, wherein the medium contains methanol.

4. The bacterium according to claim 1, wherein said DNA comprises the nucleotide sequence of SEQ ID NO: 9.

5. A method for producing L-lysine or L-arginine, comprising culturing the bacterium belonging to the genus *Methylobacillus* of claim 4 in a medium to produce and accumulate L-lysine or L-arginine in culture, and collecting L-lysine or L-arginine from the culture.

6. The method for producing L-lysine or L-arginine according to claim 5, wherein the medium contains methanol.

* * * * *